DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED DECEMBER 4, 1973

917 O.G. 8

T917,001

SYNTHESIS OF CHLORINATED BALLASTED QUINONES

Albert E. Anderson, Jr., Penfield, and Ilmari F. Salminen, Rochester, N.Y. (both % Eastman Kodak Company, Rochester, N.Y. 14650)

Filed Dec. 2, 1971, Ser. No. 204,295

Int. Cl. C07c *49/64*

U.S. Cl. 260—396 R

No Drawing. 7 Pages Specification

Chlorinated, ballasted quinones are prepared in one step in high purity and high yield by the oxidative chlorination of the corresponding ballasted p-aminophenol or quinone. Specifically,

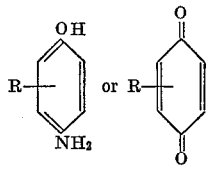

wherein R=alkyl or aryl of at least 8 carbon atoms, is treated with chlorine in the presence of a solvent mixture of acetic acid and water. The solvent mixture is preferably 70–90% by volume of acetic acid. The process is preferably carried out at a temperature of from 80–120° C. 2,3,6-trichloro-5-(n - pentadecyl)-1,4-benzoquinone is prepared by employing either 3-(n-pentadecyl)-4-aminophenol or 3-(n-pentadecyl-1,4-benzoquinone) as the starting reactant. The chlorinated ballasted quinones thus prepared are useful in preparing dye-releasing or dye precursor-releasing compounds for image transfer systems.